United States Patent [19]

Simson

[11] 4,422,459

[45] Dec. 27, 1983

[54] ELECTROCARDIOGRAPHIC MEANS AND METHOD FOR DETECTING POTENTIAL VENTRICULAR TACHYCARDIA

[75] Inventor: Michael B. Simson, Cherry Hill, N.J.

[73] Assignee: University Patents, Inc., Norwalk, Conn.

[21] Appl. No.: 353,538

[22] Filed: Mar. 1, 1982

Related U.S. Application Data

[63] Continuation of Ser. No. 208,219, Nov. 18, 1980, abandoned.

[51] Int. Cl.³ .............................................. A61B 5/04
[52] U.S. Cl. ................................................... 128/702
[58] Field of Search ............... 128/696, 699, 700, 702, 128/703, 704, 705, 708; 364/415, 417

[56] References Cited

U.S. PATENT DOCUMENTS

| | | |
|---|---|---|
| 3,605,727 | 9/1971 | Zenevich et al. .................. 128/708 |
| 3,799,147 | 3/1974 | Adolph et al. ..................... 128/700 |
| 3,822,696 | 7/1974 | Ekstrum et al. ................... 128/703 |
| 4,023,564 | 5/1977 | Valiqette et al. .................. 128/708 |
| 4,085,407 | 4/1978 | Stratbucker et al. .............. 128/699 |
| 4,115,864 | 9/1978 | Vick et al. ......................... 128/703 |
| 4,157,711 | 6/1979 | Yotam et al. ...................... 128/708 |

OTHER PUBLICATIONS

Ottonell, P., "Journal of Physics E.", vol. 7, No. 11, Nov. 1974, pp. 878–879.

Primary Examiner—William E. Kamm
Attorney, Agent, or Firm—David N. Koffsky

[57] ABSTRACT

The late portion of a post myocardial infarct patient's QRS waveform contains a high frequency signal tail which is indicative of a tendency toward vertricular tachycardia. This invention digitally processes and filters a patient's QRS signals in a reverse time manner to isolate the high frequency tail and avoid the filter ringing which would otherwise hide the signal.

16 Claims, 5 Drawing Figures

TIME = ms

ELECTROCARDIOGRAPHIC MEANS AND METHOD FOR DETECTING POTENTIAL VENTRICULAR TACHYCARDIA

This application is a continuation of application Ser. No. 208,219, filed Nov. 18, 1980 and now abandoned.

BACKGROUND OF THE INVENTION

This invention relates to electrocardiography and, more particularly, to means for analyzing a portion of an electrocardiographic signal to predict potential ventricular tachycardias.

Sudden death from acute arrhythmia is a major risk in the first few hours after a myocardial infarction. During the first few days, the incidence of ventricular arrhythmia is approximately 90%. The percentage of arrhythmias decreases considerably after the first several days but still presents a substantial risk to the myocardial infarct patient. Statistically, without treatment, approximately 50% of all infarct patients will eventually die of ventricular arrhythmia.

A reproducible and consistent ability to predict a patient's propensity for lapsing into an arrhythmia is needed. Several investigators, employing signal averaging techniques, have detected, on the body surface, small, high frequency potentials in the late QRS and ST-segments of electrocardiograms in patients and animals prone to ventricular tachycardia. (Uther, et al.: "The Detection of Delayed Activation Signals of Low Amplitude in the Vector Cardiogram of Patients with Recurrent Ventricular Tachycardia by Signal Averaging", *In Management of Ventricular Tachycardia—Role of Mexiletine,* edited by E. Sandoe, et al., Excerpta Medica, Amsterdam, 1978, pp. 80-82.) Drs. Uther, et al. found that these potentials did not occur in healthy, young people and suggested that they represented areas of delayed myocardial depolarization.

Obviously, if it can be shown that the high frequency signal in the late QRS of a myocardial infarct patient is common to most, if not all, infarct patients who are subject to ventricular tachycardia, an important new diagnostic tool would would be available. Technically, however, it is extremely difficult to isolate accurately high frequency signals late in the QRS complex. A filter must be used to eliminate the lower frequency portions. Unfortunately, substantially all filters "ring" for a period of time after application of the relatively high energy, initial portion of the QRS waveform. This ringing effectively hides any low amplitude, high frequency portions late in the QRS.

In a large clinical trial supervised by the inventor, using an electrocardiographic analysis system which will be hereinbelow described, it has been found that 92% of postmyocardial infarct patients who are subject to ventricular tachycardia, do, indeed, exhibit a distinctive high frequency signal tail in their late QRS signal. This signal is present in only 7% of post infarct patients who are free of ventricular tachycardias. In addition, it was found that a patient subject to ventricular tachycardia will exhibit a QRS signal of substantially longer duration than patients without ventricular tachycardia.

Accordingly, it is an object of this invention to provide an electrocardiographic system, capable of reliably determining the presence of absence of a high frequency segment during the late portion of a patient's QRS signal and measuring the magnitude of that segment.

It is another object of this invention to provide an electrocardiographic analysis system which is capable of determining the width of a QRS signal.

SUMMARY OF THE INVENTION

Each of a patient's X, Y, and Z electrocardiographic signals are converted from analog to digital values, processed to select only normal or typical QRS waveforms, and signal averaged over several hundred beats to obtain a relatively noise-free composite QRS. The latter portions of the X, Y, and Z digital QRS signals are then applied in reverse time order to a digital high pass filter. The reverse time processing enables the ringing artifact to be eliminated from the filter's output. The resulting filtered outputs are combined to create a composite filtered QRS, examined, and the last 40 milliseconds of the filtered composite is isolated and measured to obtain an indication of the level of high energy content. The initial portion of the QRS waveform is also processed in a forward direction to obtain an indication of its total duration.

Further features and advantages of the invention will become more readily apparent from the following detailed description, when taken in conjunction with the accompanying drawings.

DESCRIPTION OF THE PREFERRED EMBODIMENT

Figure 1:
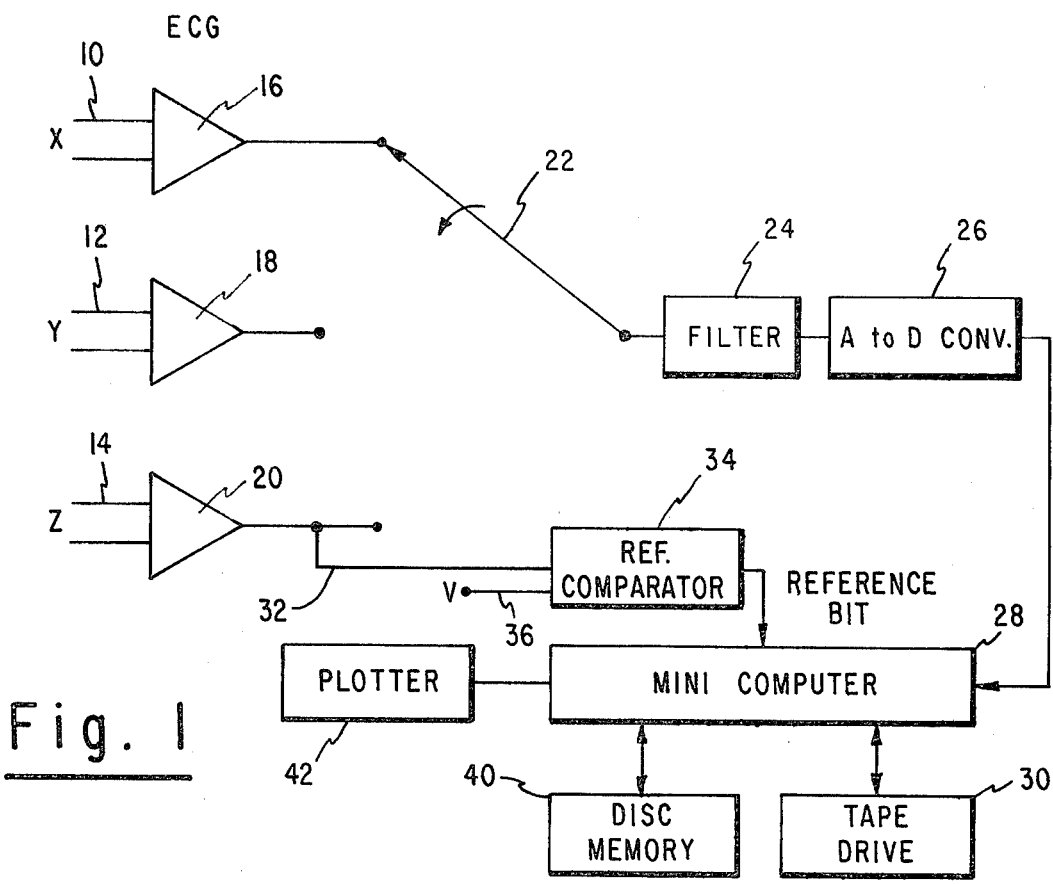
FIG. 1 is a simplified, functional, block diagram of an embodiment of the invention.

Referring now to FIG. 1, there is shown a simplified, functional, block diagram of an apparatus constructed in accordance with the invention. Each of leads 10, 12, and 14 is a bipolar electrocardiographic lead. The X lead is applied to the patient's midaxillary line at the fourth intercostal space (under the left arm between the fourth and fifth ribs). The Y electrodes are placed at the superior aspect of the sternum and the proximal left leg. The Z electrode is at the "$V_2$" position (left of sternum at the nipple line), and the other is directly posterior. Each of the respective X, Y, and Z leads (10, 12, and 14) is fed respectively to ECG amplifiers 16, 18, and 20 (Analog Devices Model 283J isolation amplifier). The output of each amplifier is passed to a switch contact, through switch 22, and to low pass filter 24. Filter 24 characteristically attenuates all signals above 250 Hz. The output from filter 24 is fed to an analog to digital converter 26 which samples the incoming voltage every millisecond and converts it to a 12-bit binary signal. (An Analog Devices Ad572 was employed and used at a sample rate of 1,000 samples per second.) The time segment outputs from A to D converter 26 are fed to minicomputer 28, which then stores the data on tape drive 30 (a Hewlett Packard 9825 desktop minicomputer was used).

The X, Y, and Z ECG signals are sequentially connected to filter 24 and A to D converter 26 by the operation of switch 22. The output from each is sampled for 133 seconds to obtain the necessary continuum of recorded signals. The output from Z ECG amplifier 20 is fed, in addition, via conductor 32 to a reference comparator 34. Also applied to reference comparator 34 is a voltage, via conductor 36 which sets the comparison level. When the QRS portion of the ECG signal appears on line 32, and it passes through voltage V, the reference comparator generates a reference bit which is recorded along with the corresponding time segment output of A to D converter 26. This reference bit enables all QRS waves to be overlaid, one on another, for selection and averaging purposes (to be discussed hereinbelow). Also connected to minicomputer 38 are disc memory 40 and plotter 42, whose functions also will be hereinafter discussed.

Figure 2:
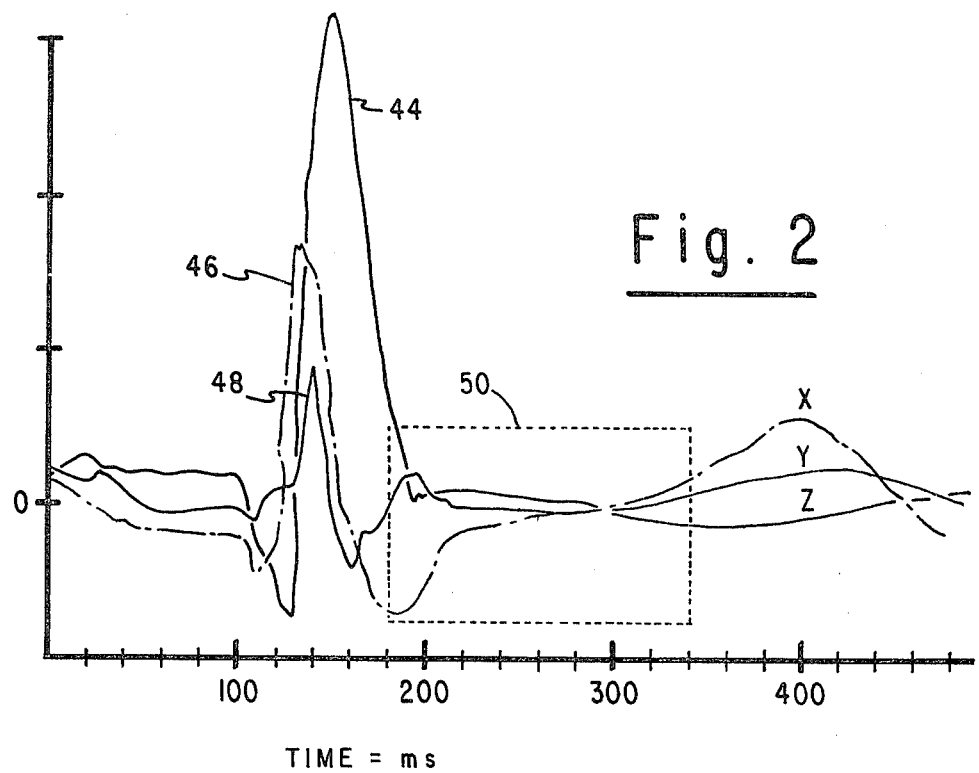
FIG. 2 is a trace-showing of the signal-averaged QRS portion of a patient's electrocardiogram.

Referring now to FIG. 2, ECG waveforms from the X, Y, and Z leads (as seen at the outputs of amplifier 16, 18, and 20) are respectively shown. Waveforms 44, 46, and 48 are the respective QRS portions of a patient's ECG as sensed by each of ECG leads 10, 12, and 14, respectively. It is the portion of the QRS waves enclosed by box 50 wherein it has been found that high frequency anomalies occur, which are indicative of an infarct patient's propensity toward ventricular tachycardia. Before the portion of the signal, appearing in box 50, can be examined, however, a number of preprocessing steps must be accomplished.

Figure 3:
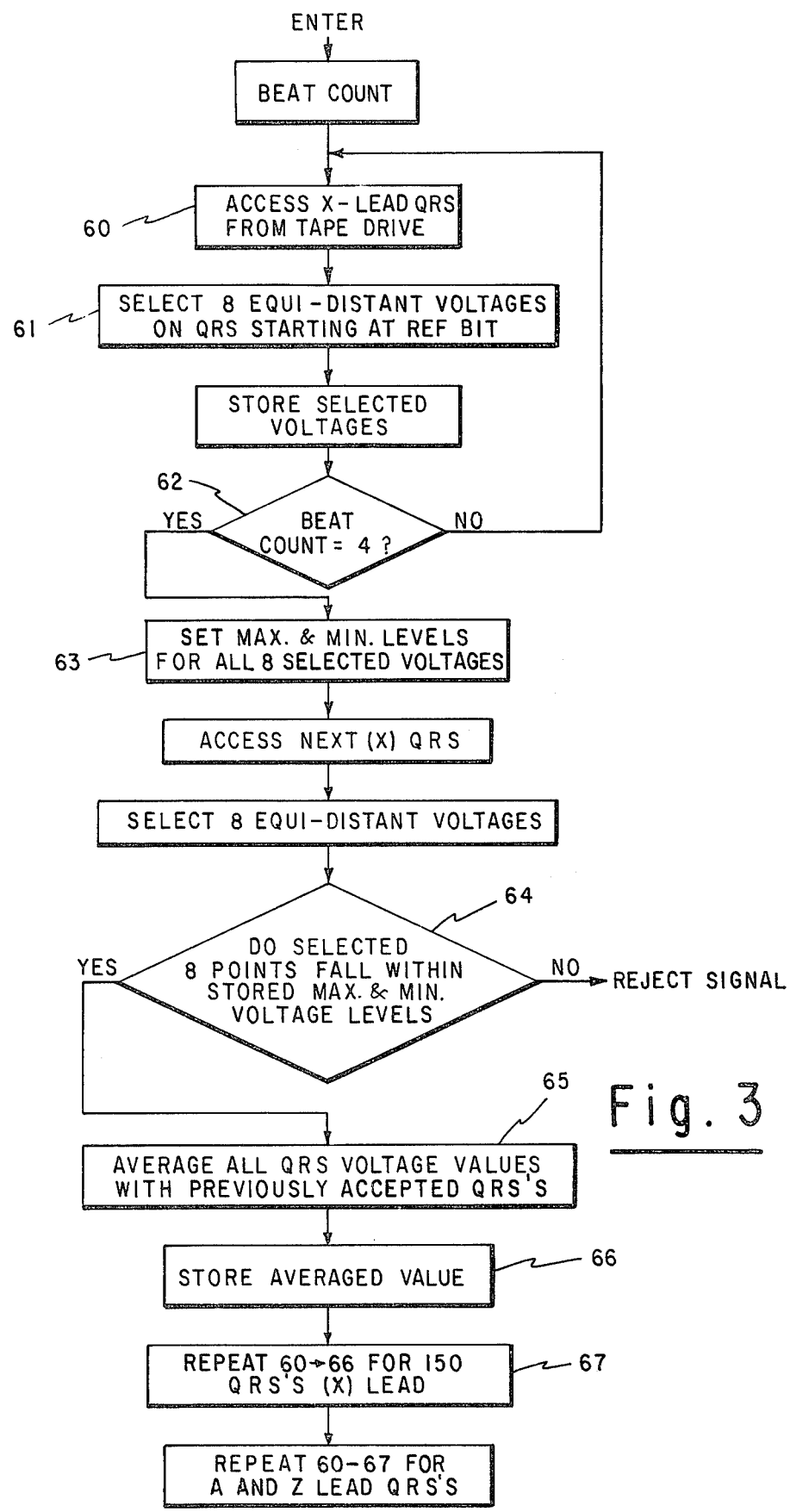
FIG. 3 is a simplified flowchart of a program utilized to implement a template selection and signal averaging routines.

Referring now to FIG. 3, there is illustrated a simplified flowchart of a computer routine utilized to implement a "template" selection and signal averaging routines. Initially, a single beat, including a QRS, is accessed from the tape drive and placed in a buffer register, as illustrated by block 60. The reference bit is here employed to grossly acquire the location of the QRS. Subsequently, eight equidistant voltage points on the QRS, starting with one at the reference bit and ending with one at 128 milliseconds, are selected and stored (box 61). This process continues for four QRS counts, as indicated by decision diamond 62, and enables the establishment of the initial template against which succeeding QRS signals will be tested. After the fourth QRS signal is stored, the maximum and minimum voltage values for each of the eight voltage points on the four recorded QRS waveforms are tabulated and become the initial template (box 63). Then, the next QRS signal is selected, its eight voltage points are determined and stored, and, as indicated in decision diamond 64, each point is selectively tested against the stored maxima and minima to determine whether it falls within or without the respective values. If it is found that there is a mismatch in any one of the eight points, the signal is rejected as not being a QRS or being some other artifact which is not of interest. If all eight points fall within the maxima and minima, the waveform is accepted as a QRS, and its 512 voltage points, spanning the accepted QRS, are then averaged with the corresponding 512 points of the previously stored QRS signals (box 65), and the resulting averaged value stored in disc memory 50 (box 66). This subroutine is repeated for 150 QRS's which are subsequently passed through the template, averaged, and then stored to accomplish a composite-averaged QRS wave for the X lead. The template voltage minimum and maximum test points may be updated during the processing to assure accurate QRS selection. The same subroutine is then repeated for the Y and Z leads, and the averaged values for each of the composite Y and Z QRS signals also are respectively stored in disc memory 40.

The above processing greatly reduces the noise inherent in the QRS signal—by the square root of the number of averaged beats—and provides three averaged QRS waveforms which are relatively noise-free and suitable for subsequent processing. Approximately 150 beats per lead are signal-averaged and recorded. At this point, the recorded QRS waveforms may be plotted out on plotter 42 for examination by the physician. The plot also enables the physician to pick out the midpoint of the QRS for the subsequent filtering step.

Figure 4:
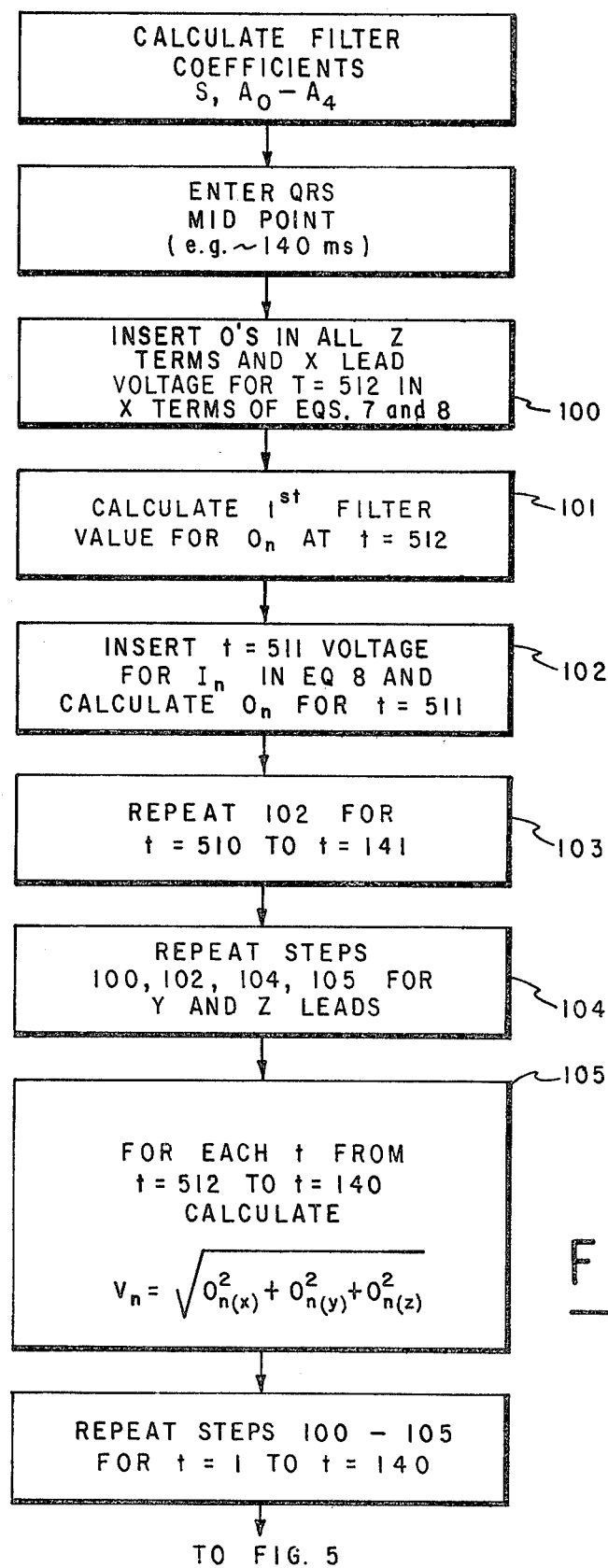
FIG. 4 is a simplified flowchart of a program for implementing a high pass digital filter.

Referring now to FIG. 4, a flowchart is shown which describes, in simplified detail, the digital filtering employed to further analyze the averaged QRS waveforms. Digital filters are well-known in the art and will not be described here in any substantial detail. Reference is made, however, to two recognized works [i.e., *Digital Signal Analysis* by S. D. Stearns, Hayden Book Company, Inc., (1975) pp. 182–222; and *Digital Signal Processing* by Oppenheim and Schafer, Prentice-Hall, Inc., (1975) pp. 195–282], the contents of both of which are incorporated herein by reference. The aforementioned excerpts teach, in detail, the methods for designing various digital implementations of analog filters. In this instance, the digital filter design employed was a four-pole, high pass, Butterworth design. While the Butterworth filter is only one of a number which can be employed, it does exhibit a maximally flat response above the corner frequency (in this case 25 Hz). It continuously attenuates signals below the corner frequency and provides reasonably smooth transitions between frequencies passed to those not passed.

Referring now to FIG. 4, the first operation which must be performed is to calculate the filter coefficients S, and $A_0$ to $A_4$. Each of the following coefficients has the following equation:

$$S = T_1^4/Q \quad \text{(equation 1)}$$
$$A_0 = 1 \quad \text{(equation 2)}$$
$$A_1 = (4T_1^4 + 2AT_1^3 - 2AT_1 - 4)/Q \quad \text{(equation 3)}$$
$$A_2 = (6T_1^4 - 2BT_1^2 + 6)/Q \quad \text{(equation 4)}$$
$$A_3 = (4T_1^4 - 2AT_1^3 + 2AT_1 - 4)/Q \quad \text{(equation 5)}$$
$$A_4 = (T_1^4 - AT_1^3 + BT_1^2 - AT_1 + 1)/Q \quad \text{(equation 6)}$$

where:

$T_0 = 500 - Fc$, where $Fc$ is the corner frequency of the filter (i.e., 25 Hz).

$$T_1 = \operatorname{Tan}\left(\frac{\pi T_0}{1{,}000}\right)$$

$$A = 2\cos\left(\frac{\pi}{8}\right) + 2\sin\left(\frac{\pi}{8}\right)$$

$$B = 2 + 4\cos\left(\frac{\pi}{8}\right) \cdot \sin\left(\frac{\pi}{8}\right)$$

$$Q = T_1^4 + AT_1^3 + BT_1^2 + AT_1 + 1$$

Each of equations 1–6 is calculated by inserting the corner frequency (Fc) of 25 Hz and calculating as above shown.

Next, the midpoint of X lead QRS is entered (i.e., it may be selected by examination of the plotted QRS or automatically by determining the most positive time voltage segment, e.g., 140 milliseconds). Subsequently the following equations are solved to carry out the filter function:

$$O'_n = S(I_n - 4X_1 + 6X_2 - 4X_3 + X_4) \quad \text{(equation 7)}$$
$$O_n = O'_n - A_1Z_1 - A_2Z_2 - A_3Z_3 - A_4Z_4) \quad \text{(equation 8)}$$

where:

$I_n$ = input value
$O_n$ = output value
$Z_4 = Z_3$ (equation 9)
$Z_3 = Z_2$ (equation 10)
$Z_2 = Z_1$ (equation 11)
$Z_1 = O_n$ (equation 12)
$X_4 = X_3$ (equation 13)
$X_3 = X_2$ (equation 14)
$X_2 = X_1$ (equation 15)
$X_1 = I_n$ (equation 16)

To commence the filter's operation, or to reset it, zeros are inserted in all Z terms of equation 8, and the voltage time segment to be filtered ($I_n$) is inserted in all X terms of equation 7 (box 100). In this case, the last time segment voltage (t=512 ms) is employed, and equations 7 and 8 are solved for the value of $O_n$ which corresponds to an input signal $I_n$ equivalent to the voltage value at t=512 (box 101). Each of the variables in equations 7 and 8 are then reset in accordance with the equalities shown in equations 9–16 and the filter routine is repeated, starting with equation 7 and proceeding backward in time, for the next preceding voltage time segment t=511 ms. This entire process is repetitively done for all segments to t=141 ms (boxes 102 & 103). Each of the calculated filter output values is stored, and the entire process repeated for the outputs from the Y and Z leads (box 104). Subsequently, a composite voltage $V_n$ is calculated in accordance with the equation $$V_n = \sqrt{O_{n(x)}^2 + O_{n(y)}^2 + O_{n(z)}^2} \quad \text{(equation 17)}$$

(box 105). The entire filter process is then repeated for the voltage samples corresponding to time segments $t_1$ to $t_{140}$.

In summary, what has been achieved to this point is the backward filtering of the composite QRS waveforms from t=512 ms through t=141 ms, and the forward filtering of the composite QRS waveforms from t=1 ms to t=140 ms. The rearward filtering avoids the ringing perturbation which would have occurred had the signal been inserted into the filter in the forward manner, and enables the late portion of the QRS to be examined for a low amplitude, high frequency signal, indicative of potential ventricular tachycardia. In addition, an averaged, filtered composite of the patient's QRS is now stored and ready for further processing.

Figure 5:
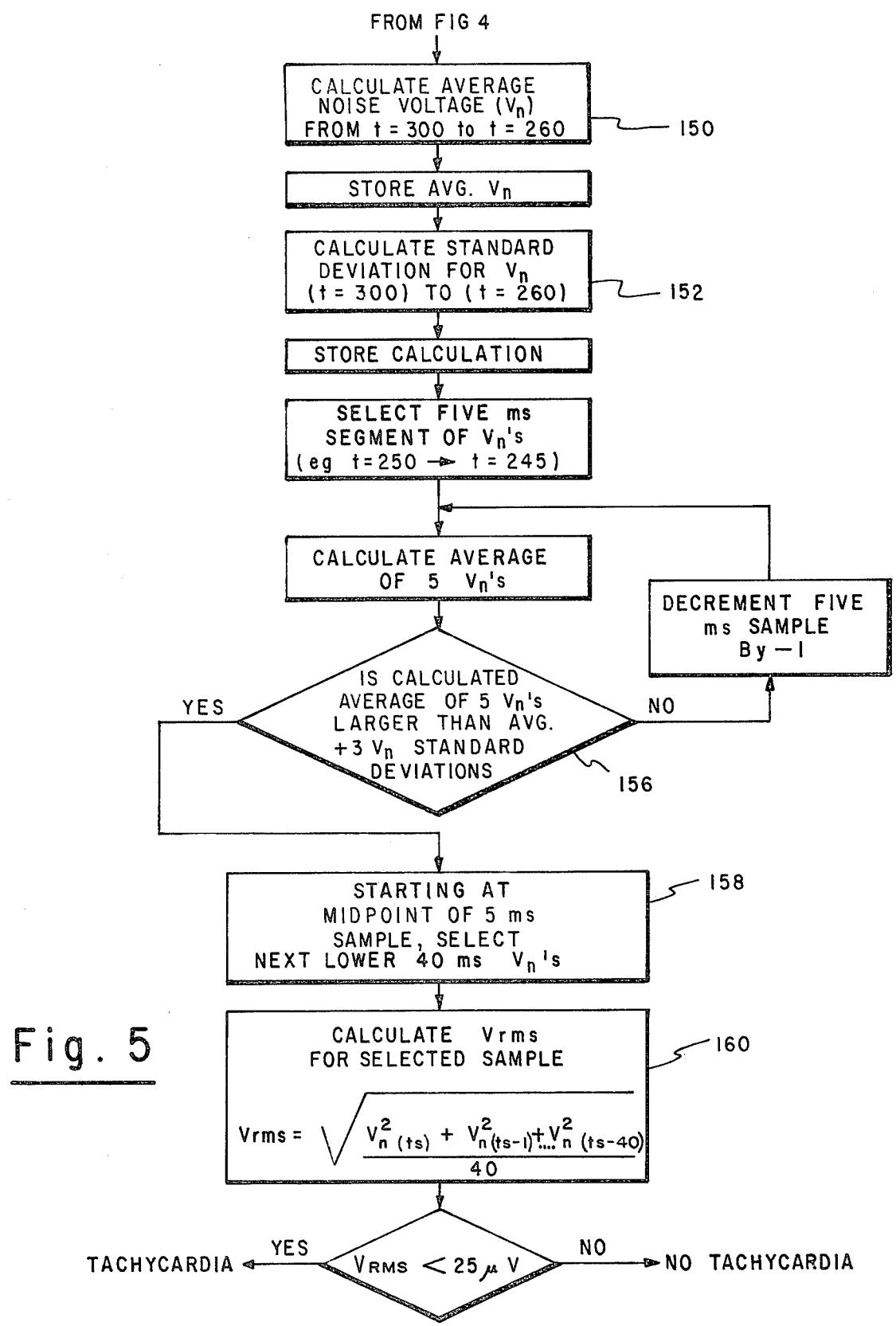
FIG. 5 is a simplified flowchart of a program for determining the last 40 millisecond portion of a filtered QRS and determining its level of high energy content.

Turning now to FIG. 5, the portion of the filtered QRS which corresponds to the late section containing the potential high frequency energy of interest is to be located. This is achieved by first (box 150) selecting a 40 millisecond sample substantially after the termination of the major portion of the QRS (e.g., t=300 ms to t=260 ms) and averaging the $V_n$ values to achieve an average noise voltage for that sample. That average noise is stored, and a standard noise level deviation is calculated (box 152) employing the following equation:

$$\text{Standard deviation} = \sqrt{\frac{\sum\limits_{n=260}^{n=300} V_n^2 - \frac{\left(\sum\limits_{n=260}^{n=300} V_n\right)^2}{40}}{39}} \quad \text{(equation 18)}$$

This standard noise deviation is stored, and a 5 millisecond sample of the QRS is selected (e.g., from t=250 ms to t=255 ms). The average value of the time segment voltages from t=250 ms to t=255 ms is calculated and compared to the average noise level plus three standard deviations previously determined. If the calculated value for the 5 millisecond sample does not exceed the total, the time segment is decremented by one time slot (i.e., one millisecond), and the process repeated until the selected average voltage of the sample does exceed the level of the calculated noise plus three standard deviations (decision diamond 156). This occurrence indicates that the selection process has arrived at the termination of the QRS signal (i.e., the middle time segment of the 5 millisecond sample is defined as the end of the QRS.)

In order to determine whether the QRS signal has or does not have the frequency tail referred to above, the voltage sample in the middle time segment ($t_s$) of the 5 millisecond sample is then selected as well as the next lower 39 voltage time segments (e.g., from t=225 to t=186), as shown by box 158. The root mean square value of all of these voltages is then calculated with equation 19 (box 160):

$$V_{RMS} = \sqrt{\frac{V_{n(t_s)}^2 + V_{n(t_s-1)}^2 + \cdots V_{n(t_s-40)}^2}{40}} \quad \text{(equation 19)}$$

The RMS voltage of the 40 ms sample is then compared to 25 microvolts, and if it exceeds 25 microvolts, it is indicative that the patient is not susceptible to ventricular tachycardia; whereas, if it is less than 25 microvolts, it is indicative that the patient is subject to ventricular tachycardia. It should be understood that the high frequency component found in patients with ventricular tachycardia extends the tail of the QRS by several tens of milliseconds, but at a relatively low level. Thus, a low level measurement indicates that there is a low level, high frequency tail of energy appended to the QRS. If the voltage exceeds the 25 microvolt level, it is indicative that, in lieu of there being the aforementioned tail of high frequency energy, the measurement is actually being made on the major portion of the QRS signal which has high levels of high frequency energy. The results of these tests can be displayed or printed out by minicomputer 28 shown in FIG. 1 for the physician's use.

It has also been found that the width of the QRS waveform has a relationship to a patient with ventricular tachycardia. In order to measure the width of the QRS in the above system, it is only necessary to obtain an indication of the beginning of the QRS waveform, as the end of the QRS has already been determined, i.e., at box 158 of FIG. 5. The initiation of the QRS is calculated in much the same manner. In specific, from t=1 to t=40, a 40-millisecond sample of noise measurements is averaged, and the standard deviation calculated. Five millisecond values are then selected and tested to determine whether the average value of each 5-millisecond sample exceeds the average noise plus three standard deviations. For the 5-millisecond sample which does exceed that level, the beginning of the QRS is then defined as the middle time segment of that 5-millisecond segment. The duration of the QRS then stretches from the middle of that segment to the end of the QRS as defined above.

The above-mentioned apparatus was employed in a substantial clinical test at the Cardiovascular Section, Hospital of the University of Pennsylvania, Philadelphia, Pa. Twenty-seven control patients and 39 patients with ventricular tachycardia were studied. All patients had had myocardial infarctions, were off anti-arrhythmic drugs, and did not have bundle branch block. The 39 patients with ventricular tachycardia had either sustained or inducible ventricular tachycardia. The QRS duration was found to be longer in patients with ventricular tachycardia, i.e., 139 milliseconds±26 ms vs. 95 milliseconds±10 ms. Seventy-three percent of the patients with ventricular tachycardia had a QRS duration longer than 120 milliseconds, but none of the control group did. The filtered QRS voltage revealed that patients with ventricular tachycardia had a low amplitude and slowly declining high frequency signal at the end of the QRS. In contrast, the control group had a different high frequency energy distribution; the high frequency voltage at the end of the QRS was of larger amplitude but ended abruptly. Ninety-two percent of the patients with ventricular tachycardia had less than 25 microvolts of high frequency energy in the last 40 milliseconds of the QRS; only 7% of patients without ventricular tachycardia had less than 25 microvolts in this segment. On average, the control patients exhibited a 74 microvolt RMS level, whereas the ventricular tachycardia patients exhibited a 15 microvolt level. In summary, this study of the high frequency voltage in the late QRS identified patients with ventricular tachycardia after myocardial infarction, with a 92% sensitivity and a 93% specificity.

While the invention has been illustrated with respect to specific hardware, it should be understood that alternative general or specific purpose computing equipment or hard wired logic circuitry could be used in practicing the invention.

I claim:

1. A method for analyzing electrocardiograph signals to determine the presence or absence of a predetermined level of high frequency energy in the late QRS signal, comprising the steps of:
    converting a series of QRS signals to time segments, each segment having a digital value equivalent to the analog value of said signals at said time;
    applying a portion of said time segments in reverse time order to high pass filter means;
    determining an arithmetic value of the amplitude of the output of said filter; and
    comparing said value with said predetermined level.

2. The method of claim 1 further including the step of generating a presence or absence signal which is a function of said comparison.

3. The method of claim 1 further including the step of averaging the digital values of said series of QRS signals to obtain an averaged composite QRS signal before the application thereof to said high pass filter means.

4. The method of claim 3 wherein said portion of said time segments includes the last 40 milliseconds of the averaged QRS signal.

5. The method of claim 4 wherein said arithmetic value is the root mean square.

6. The method of claim 2 further including the step of measuring the duration of said averaged QRS signal.

7. Apparatus for analyzing electrocardiograph signals to determine the level of high frequency energy in the late QRS signal comprising:
    means for converting X, Y, and Z lead electrocardiographic input signals to digital valued time segments;
    means for examining said X, Y, and Z digital valued time segments and selecting therefrom the QRS waveform portions thereof;
    means for signal averaging a multiplicity of said selected QRS waveforms for each of said X, Y, and Z inputs and providing composite, digital X, Y, and Z QRS waveforms;
    high pass filter means;
    means for applying to said filter means, in reverse time order, the anterior portion of each said digital X, Y, and Z waveform; and
    means for comparing the output of said filter means with a predetermined level to obtain an indication of the presence of a high frequency, low level, energy component in the filter output of said anterior portions.

8. The invention as defined in claim 7 wherein said comparing means examines only a portion of said filter's output.

9. The invention as defined in claim 8 wherein said portion of said filter's output represents the filtered last 50 milliseconds of the QRS waveform.

10. The invention as defined in claim 9 wherein said comparing means combines selected portions of said filter's output for each of the X, Y, and Z signals and calculates the root mean square value of said combined portions.

11. The invention as defined in claim 10 further comprising:
    means for applying to said filter means, in forward time order, the early portion of each said digital X, Y, and Z QRS waveforms;
    means for extracting from said filter's output the time of commencement of said QRS waveform; and
    means responsive to said extraction means and said comparing means for determining the width of said QRS waveform.

12. Apparatus for analyzing electrocardiograph signals comprising:
    means for converting electrocardiographic input signals to digital QRS waveform segments;
    high pass filter means:
    means for applying to said filter means, in reverse time order, the anterior portion of each said digital QRS waveform; and
    means for comparing the output of said filter means with a predetermined level.

13. The invention as defined in claim 13 wherein said means for comparing examines only a portion of said filter's output.

14. The invention as defined in claim 13 wherein said portion of said filter's output represents the filtered last 50 milliseconds of the QRS waveform.

15. The invention as defined in claim 13 wherein said means for comparing combines selected portions of said filter's output and calculates the root mean square value of said combined portions.

16. The invention as defined in claim 12 or 15 further comprising:

means for applying to said filter means, in forward time order, the early portion of each digital QRS waveform;

means for extracting from said filter's output the time of commencement of said QRS waveform; and means responsive to said extraction means and said means for comparing for determining the width of said QRS waveform.

* * * * *

UNITED STATES PATENT AND TRADEMARK OFFICE
CERTIFICATE OF CORRECTION

PATENT NO. : 4,422,459
DATED : December 27, 1983
INVENTOR(S) : Michael B. Simson It is certified that error appears in the above-identified patent and that said Letters Patent is hereby corrected as shown below:

Cover page, Column 2, in references cited, delete "Valiqette", and insert --Valiquette--.

Column 1, line 44, delete "would", first occurrence.

Column 1, line 66, delete "of", first occurrence, and insert --or--.

Column 6, line 33, after "calculated", insert --in accordance--.

Claim 13, line 1, delete "13", and insert --12--.

Signed and Sealed this

Twenty-fifth Day of October, 1988

Attest:

DONALD J. QUIGG

*Attesting Officer*  *Commissioner of Patents and Trademarks*